(12) United States Patent
Uchida et al.

(10) Patent No.: US 8,721,079 B2
(45) Date of Patent: May 13, 2014

(54) FUNDUS CAMERA

(75) Inventors: Koji Uchida, Utsunomiya (JP); Satoshi Aikawa, Yokohama (JP); Yasuhiro Dobashi, Matsudo (JP)

(73) Assignee: Canon Kabushiki Kaisha, Tokyo (JP)

( * ) Notice: Subject to any disclaimer, the term of this patent is extended or adjusted under 35 U.S.C. 154(b) by 3 days.

(21) Appl. No.: 13/532,478

(22) Filed: Jun. 25, 2012

(65) Prior Publication Data
US 2012/0327366 A1 Dec. 27, 2012

Related U.S. Application Data

(63) Continuation of application No. 12/849,618, filed on Aug. 3, 2010, now Pat. No. 8,226,234.

(30) Foreign Application Priority Data

Aug. 6, 2009 (JP) .................. 2009-183339

(51) Int. Cl.
*A61B 3/14* (2006.01)
*A61B 3/10* (2006.01)
*A61B 3/15* (2006.01)

(52) U.S. Cl.
CPC ..................... *A61B 3/152* (2013.01)
USPC ........................ 351/208; 351/206; 351/221

(58) Field of Classification Search
USPC ............................ 351/206, 208, 221; 396/18
See application file for complete search history.

(56) References Cited

FOREIGN PATENT DOCUMENTS

| JP | 03-001835 A | 1/1991 |
| JP | 09-094229 A | 4/1997 |
| JP | 2004-147826 A | 5/2004 |
| JP | 2004-351151 A | 12/2004 |

*Primary Examiner* — Jack Dinh
(74) *Attorney, Agent, or Firm* — Canon U.S.A., Inc., IP Division

(57) ABSTRACT

An ophthalmologic apparatus including an index projection unit to project an index on a cornea of a subject's eye, an imaging unit to form an image on an imaging plane via an objective lens and capture an image of the index projected on the cornea, and a control unit to control a distance between the subject's eye and the object lens so that a size of the captured index becomes a predetermined size.

11 Claims, 11 Drawing Sheets

FUNDUS CAMERA

CROSS REFERENCE TO RELATED APPLICATIONS

This application is a Continuation of U.S. patent application Ser. No. 12/849,618 filed Aug. 3, 2010, which claims priority to Japanese Patent Application No. 2009-183339 filed Aug. 6, 2009, both of which are hereby incorporated by reference herein in their entireties.

BACKGROUND OF THE INVENTION

1. Field of the Invention

The present invention relates to a fundus camera which performs alignment while observing an operation distance index.

2. Description of the Related Art

In a conventional fundus camera, when an operator photographs a fundus image, a light flux is projected from the periphery of a pupil of a subject's eye, and a fundus reflection light flux is taken out from a center of the pupil as a photographing light, so that a photographing light flux has a small diameter. Thus, if the light flux deviates even a little, the pupil shades the light flux, so that a flare easily enters in an imaging plane. For performing correct positioning, it is necessary to stabilize a fixation, match a light axis of the subject's eye and an optical axis of a fundus camera optical system, and adjust alignment to a proper position.

Japanese Patent Application Laid-Open No. 62-34530 discusses a fundus camera which projects an alignment index on a cornea of a subject's eye, and determines whether the alignment index is on a proper alignment position in a state that an alignment image which is a reflection image of the projected alignment index in focus. Japanese Patent Application Laid-Open No. 7-31590 discusses a fundus camera which projects an alignment index on a cornea of a subject's eye, and determines whether the alignment index is on a proper alignment position based on separation or matching of an alignment image.

Japanese Patent Application Laid-Open No. 7-31590 and Japanese Patent Application Laid-Open No. 2000-287934 discuss a technique for moving a light guide for projecting an operation distance index. In this technique, the light guide is moved so that a proper operation distance when a fundus peripheral part is photographed is becomes longer than the proper operation distance when a fundus center part is photographed. However, this operation is not for detecting the operation distance.

In the above described conventional fundus cameras, since a light emitting diode (LED) light source having one kind of single wavelength is used as a light source for an alignment index, it can be determined whether the alignment index is in a proper alignment position or not. However, it cannot be determined whether the fundus camera is in a near position with respect to a subject's eye or in a far position in the proper alignment position.

Therefore, for operating the fundus camera to a proper alignment position, an operator moves the fundus camera once toward either direction of closing to or separating from the subject's eye, and determines a direction for closing to the proper alignment position based on whether a defocusing degree and a separation degree increase or not. There is no problem when an operator can move the fundus camera to a right direction for alignment by chance. However, when the operator moves the fundus camera toward an inverse direction, the operation for moving the camera is wasteful.

SUMMARY OF THE INVENTION

The present invention relates to a fundus camera which can perform alignment easily.

According to an aspect of the present invention, a fundus camera includes an illumination optical system configured to project a ring-shaped illumination light on a pupil of a subject's eye, an imaging optical system configured to form a fundus image of the illumination light from a fundus on an imaging plane via an objective lens, an index projection unit configured to project an operation distance index on a cornea of the subject's eye via the objective lens, an imaging unit configured to capture a reflection image from the fundus and a reflection image of the operation distance index from the cornea, a driving unit configured to move the operation distance index in an optical axis direction of the imaging optical system, an index shape recognition unit configured to recognize an index shape projected on the cornea according to a movement of a light emitting surface of the index projection unit by the driving unit, and a detection unit configured to detect operation distances of the illumination optical system and the imaging optical system with respect to the subject's eye based on driving information about the driving unit and an output of the index shape recognition unit.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
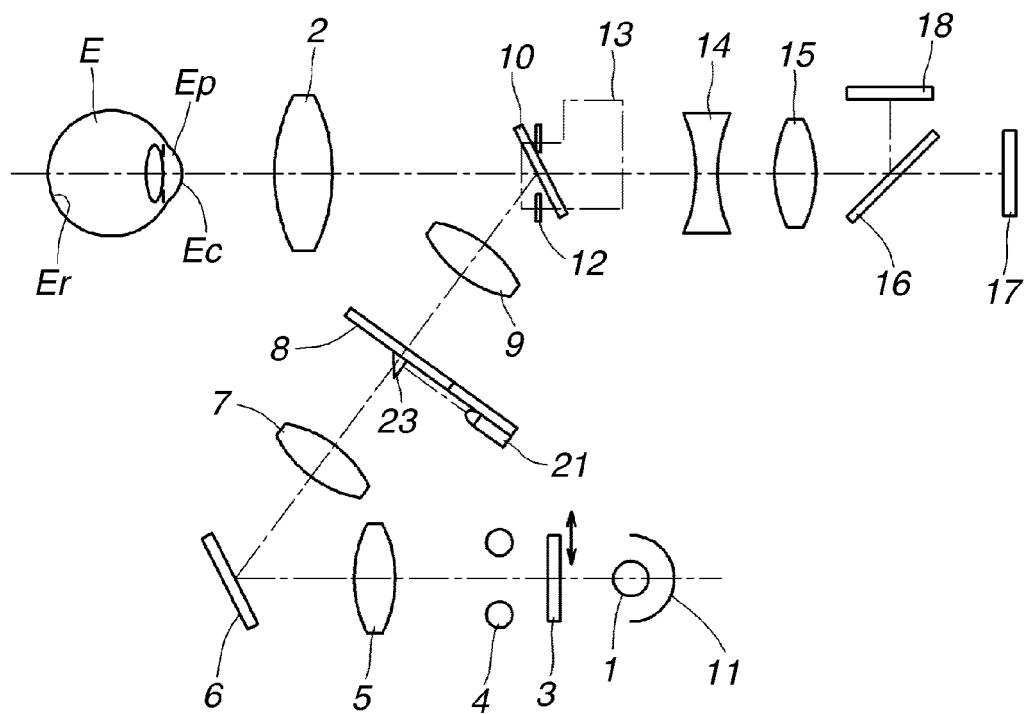
FIG. 1 illustrates an optical configuration of a fundus camera.

FIG. 1 illustrates an optical configuration of a fundus camera according to a first exemplary embodiment.

The fundus camera includes an illumination optical system from a halogen lamp 1 which is a light source for observation to an objective lens 2 in front of a subject's eye. A visible cut filter 3 which can be inserted into and removed from an optical path, a flash tube 4 which is a light source for photographing, a lens 5, and a folding mirror 6 are aligned in front of the halogen lamp 1. In a reflection direction of the folding mirror 6, a first relay lens 7, a split projection unit 8 for focusing, a second relay lens 9, and a perforated mirror 10 are aligned in this order. A hemispherical reflection mirror 11 is provided behind the halogen lamp 1.

A photographic diaphragm 12 is provided at a hole portion of the perforated mirror 10. In a imaging optical system behind the photographic diaphragm 12, an operation distance index projection unit 13 for detecting an operation distance with respect to a subject's eye E, a focus lens 14 for focusing on a fundus surface, an imaging lens 15, a quick return mirror 16 for reflecting a part of a visible light, and an imaging unit 17 are aligned. Further, in a reflection direction of the quick return mirror 16, a LED is provided in a matrix state, and an internal fixation target 18 guiding a line-of-sight direction of the subject's eye is arranged.

Figure 2A:
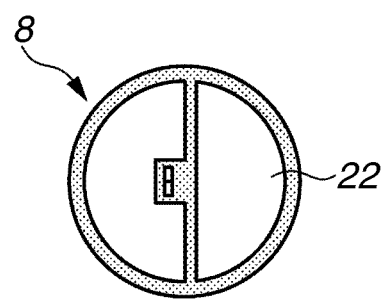
FIGS. 2A and 2B are a front view and a side view of a split projection unit.
Figure 2B:

FIGS. 2A and 2B illustrate a plane view and a side view of the split projection unit 8. The split projection unit 8 includes a split index light source 21, an infrared light transmitting body 22, and a split prism 23 formed on the infrared light transmitting body 22. The split projection unit 8 can be inserted into and removed from an illumination optical path by a split driving motor 24. The split index light source 21 includes an LED light source which emits near infrared light having a wavelength of 700 nm, and projects the infrared light to the split prism 23 from a direction approximately vertical to the illumination optical path.

The split prism 23 is formed at a center part of the optical path, and split light is projected to the illumination optical path through the split prism 23. When the split light focuses on a fundus Er, two base lines of the split light become a straight line. When the split light does not focus on the fundus Er, the base line is divided into two. The split projection unit 8 is inserted into the illumination optical path at the time of observation, and retreats immediately from the illumination path at the time of photographing.

Figure 3A:
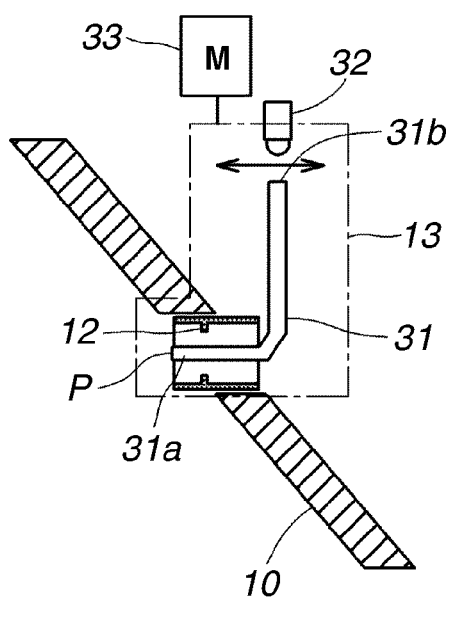
FIGS. 3A and 3B are a side view and a front view of an operation distance index projection unit.
Figure 3B:
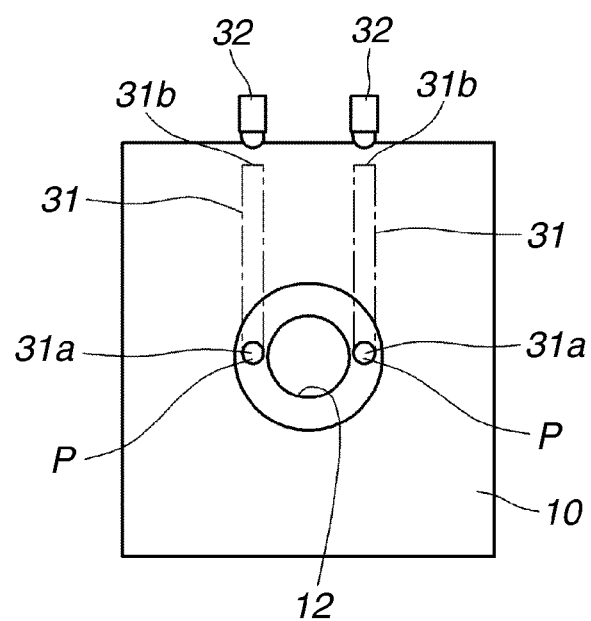

FIGS. 3A and 3B are a side view and a front view of the operation distance index projection unit 13 which is an index projection unit. Outgoing ends 31a of two light guides 31 are arranged on both sides of the photographic diaphragm 12 in the hole portion of the perforated mirror 10. Distance index light sources 32 including a near infrared light LED are provided at each incident end 31b of the light guides 31. The operation distance index projection unit 13 can be moved back and forth with a minute movement by a predetermined amount in the optical axis direction of the imaging optical system by a driving unit of a distance index driving motor 33.

An infrared light entered from the incident end 31b of the light guide 31 travels in a straight line, is reflected and changed an angle on the reflection surface, travels straight, and exits from a light emitting surface P of the outgoing end 31a. The light emitting surface P is in a conjugate relationship with the objective lens 2 to generate a virtual image P' between a cornea Ec of the subject's eye E and a crystalline lens.

Figure 4:
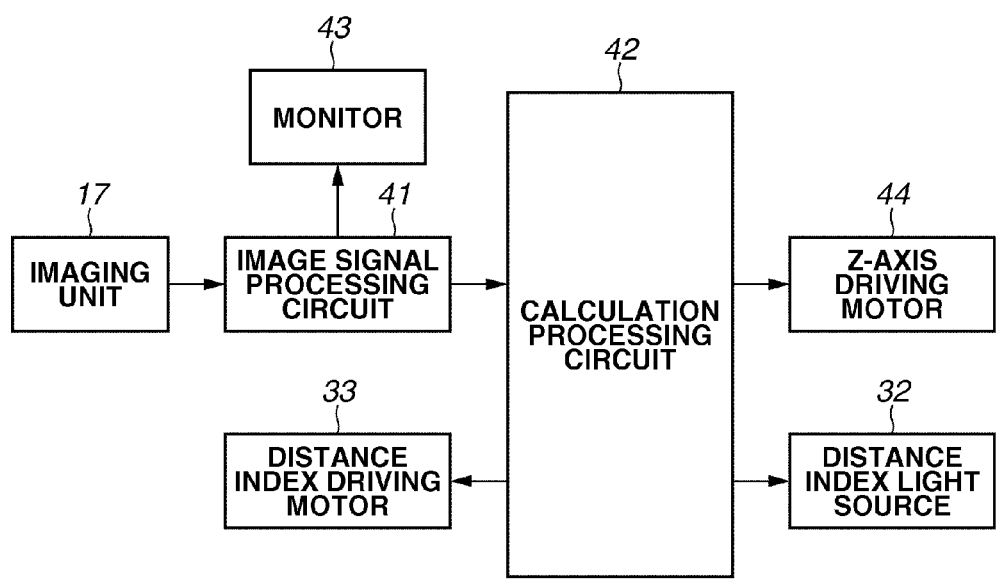
FIG. 4 illustrates a block circuit configuration according to a first exemplary embodiment.

FIG. 4 illustrates a block circuit configuration of an electric circuit unit. An output of the imaging unit 17 is connected to a calculation processing circuit 42 and a monitor 43 via an image signal processing circuit 41. Outputs of the calculation processing circuit 42 are connected to the distance index light source 32 and the distance index driving motor 33 of the operation distance index projection unit 13, and a Z-axis driving motor 44 for driving the fundus camera in the optical axis direction of the imaging optical system.

Figure 5:
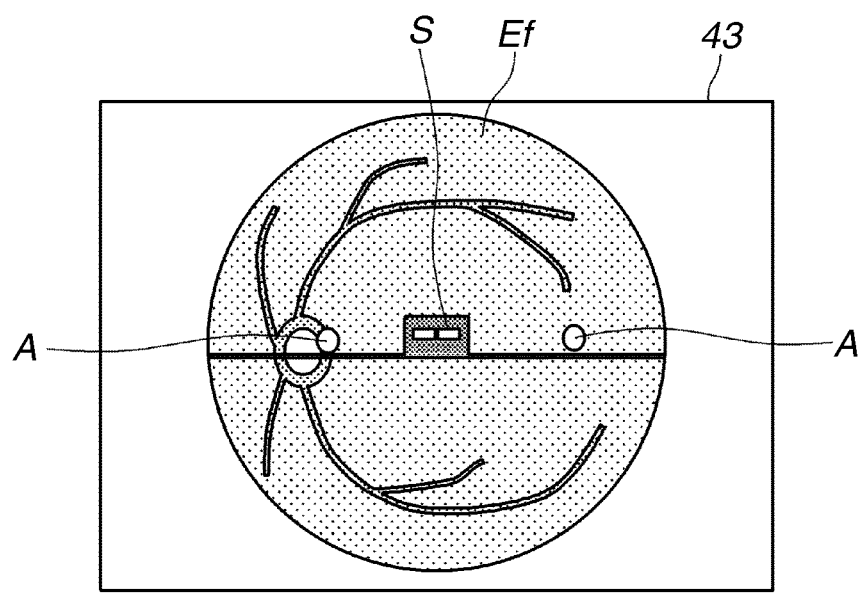
FIG. 5 illustrates an image projected on a monitor.

At the time of alignment with respect to the subject's eye E, a light flux emitted from the halogen lamp 1 is made to be infrared light by the visible cut filter 3, travels through the flash tube 4 and the lens 5, and reaches the folding mirror 6. The infrared light reflected by the folding mirror 6 travels through the first relay lens 7, the split projection unit 8, and the second relay lens 9, and enters into the perforated mirror 10. The light flux reflected by the perforated mirror 10 forms a ring light on a pupil of the subject's eye E through the objective lens 2, and illuminates the fundus Er of the subject's eye E, as infrared light. The reflection light reflected on the fundus Er passes a center of the ring light on the pupil, and passes an inside of the perforated mirror 10 through the objective lens 2. Then, the reflection light forms an image on the photographic diaphragm 12, the focus lens 14, the imaging lens 15, and the imaging unit 17, and is displayed on the monitor 43 illustrated in FIG. 5 as a fundus image Ef.

In the split projection unit 8, an infrared light emitted from the split index light source 21 is refracted in a direction of the illumination optical path by the split prism 23 arranged on the illumination optical path, travels through the perforated mirror 10 and the objective lens 2, and is projected on the fundus Er. A split image S projected on the fundus Er is captured by the imaging unit 17 via the imaging optical system. On the monitor 43, a base line is displayed at a center of the fundus image Ef, and is divided into two according to a movement of the focus lens 14. When the base line becomes one, the fundus image Ef comes into focus. An operator can determine frontward defocusing or backward defocusing based on a dividing direction of the two base lines.

In the operation distance index projection unit 13, the operation distance index is projected on the subject's eye E from two light emitting surfaces P, and a cornea reflection image with two bright spot images A is formed on the surface of the cornea Ec. The bright spot images A are formed on the imaging unit 17 and displayed on the monitor 43. In a proper alignment state, the bright spot images A are projected on positions separated from each other by a predetermined distance in a center horizontal direction of the fundus image Ef.

Figure 6:
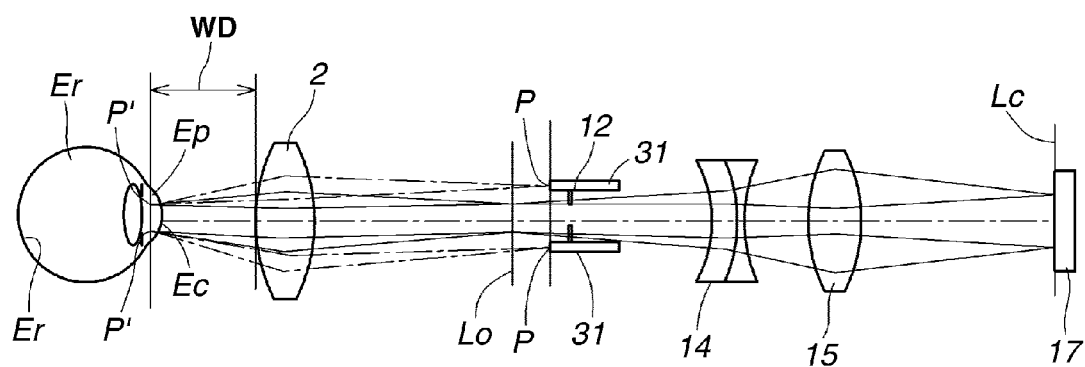
FIG. 6 illustrates an optical path of an operation distance detection optical system.

FIG. 6 illustrates an optical path of an operation distance detection optical system. The infrared light emitted from the light emitting surface P of each light guide 31 travels through the objective lens 2, is refracted at the cornea Ec of the subject's eye E and forms the virtual image P'. The virtual image P' is in a conjugate positional relationship with a primary image forming surface Lo through the objective lens 2. The fundus Er is also in a conjugate positional relationship with the primary image forming surface Lo with respect to the objective lens 2. Further, the primary image forming surface Lo is in a conjugation relationship with the imaging unit 17 with respect to the focus lens 14 and the imaging lens 15.

In such an optical configuration, a light flux emitted from the light emitting surface P of the light guide 31 is reflected on the cornea Ec, and becomes the bright spot image A. Then, the bright spot image A passes through the photographic diaphragm 12 in the perforated mirror 10, and forms an image on the imaging unit 17 via the focus lens 14 and the imaging lens 15. A light flux from the illumination optical system becomes a reflection image on the fundus Er, passes through the photographic diaphragm 12, and is projected on an imaging plane Lc of the imaging unit 17 via the focus lens 14 and the imaging lens 15. Therefore, an image formed on the imaging plane Lc is an image combined with the split image S and two bright spot images A of the operation distance index in the fundus image Ef.

The calculation processing circuit 42 outputs an amount of movement having a predetermined cycle as a driving command to the distance index driving motor 33 via the motor driver. The distance index driving motor 33 moves the light emitting surface P of the light guide 31 minutely back and forth in the optical axis direction. The bright spot images A formed on the imaging unit 17 are extracted by the image signal processing circuit 41. The distance index light source 32 of the operation distance index projection unit 13 is blinked under control of the calculation processing circuit 42. The image signal processing circuit 41 calculates a difference between images at a time of turning on and at a time of turning off of the distance index light source 32, and extracts the bright spot image A. Then, the image signal processing circuit 41 calculates an index shape, i.e., a size, of the bright spot image A, and recognizes the index shape. The light emitting surface P is automatically moved minutely back and forth by the predetermined amount in the optical axis direction.

Figure 7:
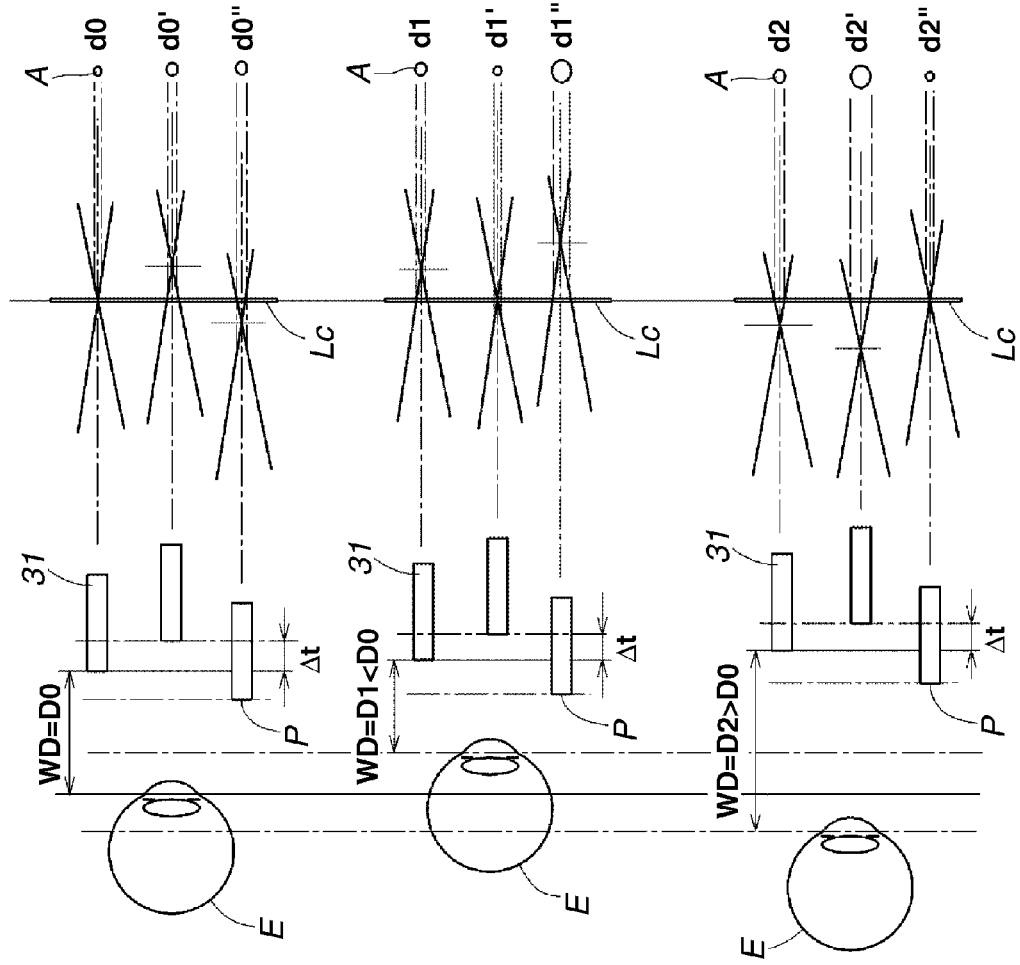
FIGS. 7A to 7C illustrate a relationship between positions of a light emitting surface and an imaging plane, and a size of a bright spot image.

FIGS. 7A to 7C illustrates a relationship between positions of the light emitting surface P and the imaging plane Lc, and the size of the bright spot image A. FIG. 7A illustrates a relationship of the shape, i.e. the size of the bright spot image A with respect to a positional deviation Δt of the light emitting surface P by the minute back and forth movement, when a positional relationship between an optical unit with a built-in optical system of the fundus camera and the subject's eye E is a proper distance (WD=D0).

When the light emitting surface P moves in the optical axis direction, the size and blur of the bright spot image A projected on the imaging plane Lc change. In a state of a proper operation distance D0, when the positional deviation Δt occurs, the size of the bright spot image A becomes large and blurred (d0<d0'=d0").

FIG. 7B illustrates the relationship of the size of the bright spot image A with respect to the positional deviation Δt of the light emitting surface P when the positional relationship between the optical unit and the subject's eye E closes more than the proper distance, i.e., when the operation distance is short which is WD=D1<D0.

In this case, when the light emitting surface P moves to the subject's eye E side in the optical axis direction, the bright spot image A is formed on a position further away from the imaging plane Lc, so that the bright spot image A becomes further largely blurred. Or when the light emitting surface P moves to the imaging plane Lc side in the optical axis direction, the bright spot image A is projected further small and vividly because the light emitting surface P closes to the imaging plane Lc (d1'<d1<d1").

FIG. 7C illustrates the relationship of the size of the bright spot image A with respect to the positional deviation Δt of the light emitting surface P when the positional relationship between the optical unit and the subject's eye E is separated more than the proper distance, i.e., when the operation distance is long which is WD=D2>D0.

In this case, when the light emitting surface P moves to the subject's eye E side in the optical axis direction, the bright spot image A is formed on a position closer to the imaging plane Lc, so that the bright spot image A is projected further small and vividly. Further, when the light emitting surface P moves to the imaging plane Lc side in the optical axis direction, the bright spot image A becomes further largely blurred because the light emitting surface P separates from the imaging plane Lc (d2"<d2<d2').

Accordingly, while the positional relationship between the optical unit of the fundus camera and the subject's eye E changes, the light emitting surface P of the light guide 31 is moved minutely back and forth by the distance index driving motor 33. Accordingly, it can be determined whether the optical unit comes closer to or is separated from the proper operation distance D0 by detecting the relationship of the size of the bright spot image A in a moving direction or the like of the distance index driving motor 33.

A detected result is displayed on the monitor 43, and an operator can recognize a direction to move and adjust the position of the optical unit back and forth. However, operability can be better that the optical unit is automatically positioned at the proper operation distance based on the detected result of the bright spot image A. In the block circuit configuration in FIG. 4, the fundus camera is driven in the operation distance direction via the Z-axis driving motor 44, based on the direction detected by the calculation processing circuit 42 and a method for detecting a movement amount described below.

Figure 8:
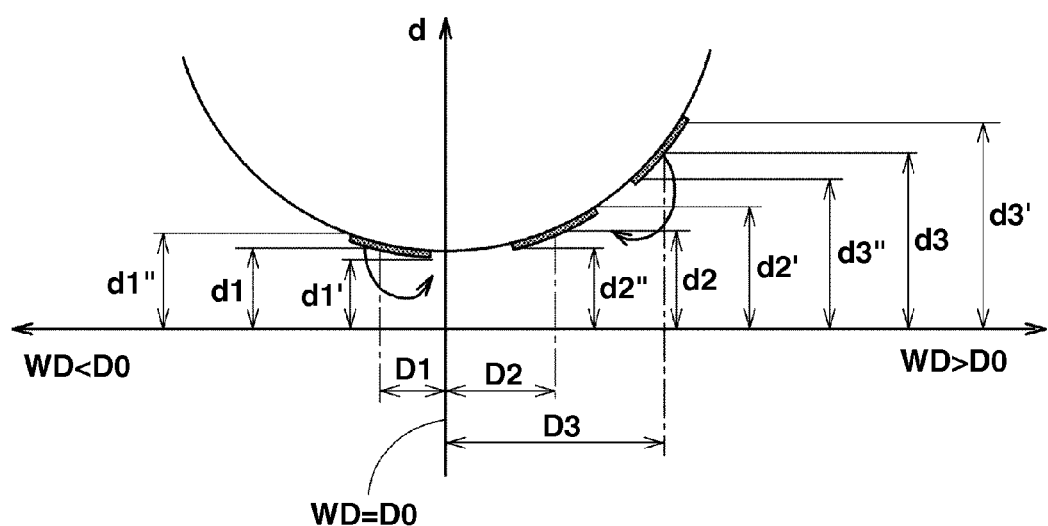
FIG. 8 is a graph illustrating a relationship between an operation distance and a size of a bright spot image.

FIG. 8 is a graph illustrating a relationship between a size d of the bright spot image A in a vertical axis and a deviation Dt with respect to the proper operation distance WD=D0 of the optical unit in a horizontal axis. In the operation distance D2 where the operation distance WD is larger than the proper distance W0, when the light emitting surface P is minutely moved in a reciprocation period, the size of the bright spot image A changes as described above, so that the relationship becomes d2"<d2<d2'.

In the relationship of d2'−d2">0, control is performed to move the optical unit closer to the proper operation distance D0 by a specific amount in proportion to a ratio of d2'/d2". When the operation distance WD has a value D3 which is larger than a value D2, the control to move the optical unit closer to the proper operation distance D0 can be performed similarly.

When the operation distance WD has a value D1 which is smaller than a value of the proper distance D0, the relationship becomes d1'−d1"<0, so that the control is performed to move the optical unit closer to the proper operation distance D0 by a specific amount in proportion to a ratio of d1"/d1' in an inverse direction. By this operation, the optical unit can be driven in the proper operation distance D0. Therefore, the operation distance WD can be detected by the movement of the light emitting surface A and the recognition and determination of the bright spot image A.

Figure 9:
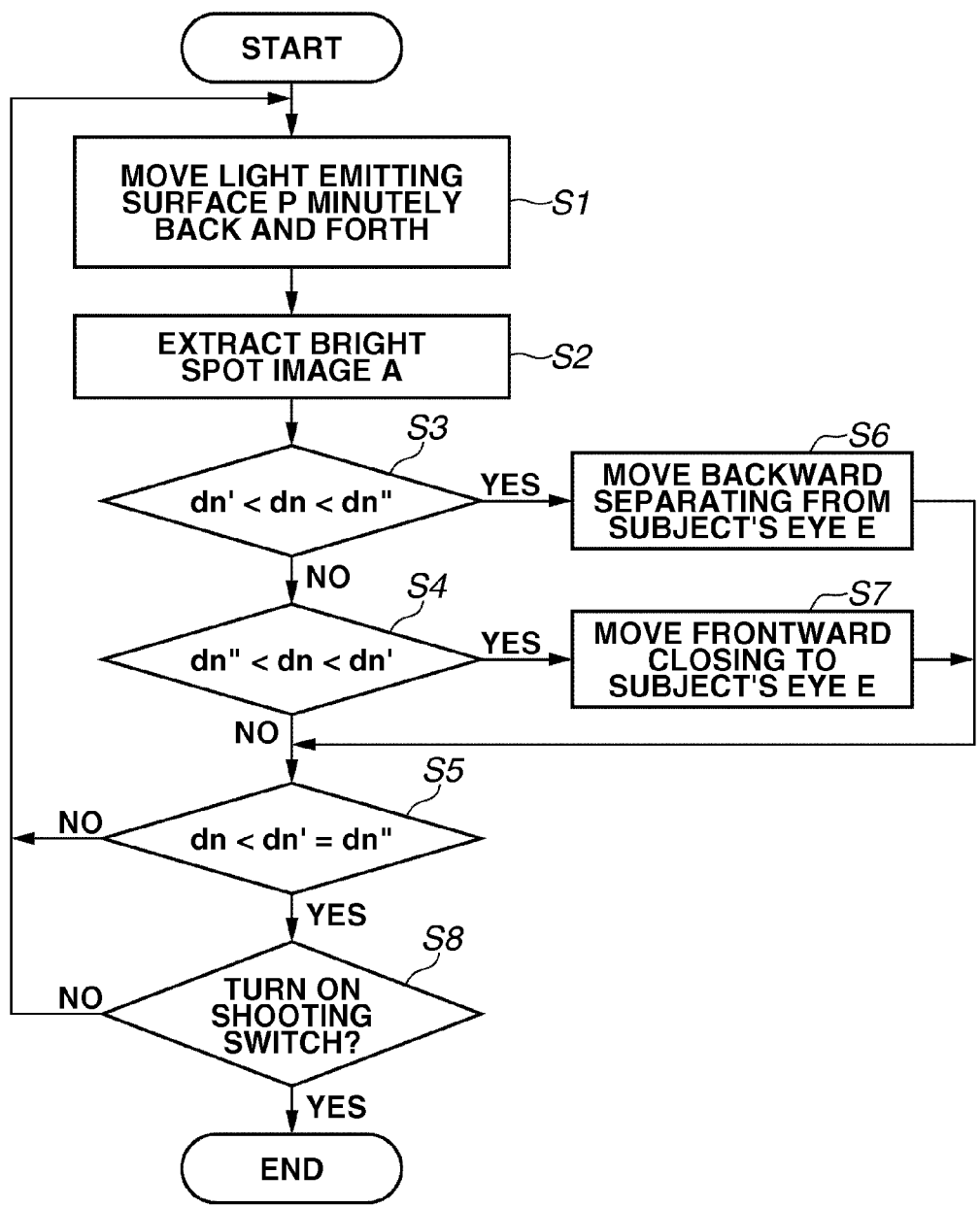
FIG. 9 is a control flowchart for detecting a bright spot.

FIG. 9 is a flowchart illustrating processing for associating the recognition of the bright spot image A which is a projection index and driving information about the operation distance. The image signal processing circuit 41 extracts the bright spot image A received by the imaging unit 17. In step S1, when the bright spot image A is extracted, the driving unit minutely moves the light emitting surface P back and forth of a predetermined amount. In step S2, the image signal processing circuit 41 extracts the bright spot images at a center and maximum positions in back and forth directions of the reciprocation movement of the light emitting surface P. In steps S3 to S5, a state of the optical unit is determined according to the size of the bright spot image A based on FIGS. 7A to 7C and FIG. 8.

More specifically, when dn"<dn<dn' is satisfied (YES in step S3), then in step S6, the optical unit is moved backward so as to separate from the subject's eye E, and processing proceeds to step S5. When dn"<dn<dn' is satisfied (YES in step S4), then in step S7, the fundus camera is moved forward so as to come closer to the subject's eye E, and processing proceeds to step S5. In step S5, when dn<dn'=dn" is satisfied (YES in step S5), it is determined that the fundus camera is at the proper operation distance D0, and the fundus camera enters into a shooting standby state. In step S8, the operator pushes a shooting switch to perform shooting (YES in step S8), and processing ends. In step 5, when dn<dn'=dn" is not satisfied (NO in step S5), the processing returns to step S1, and the processing in the flow is repeated again.

When a fundus is photographed, the split projection unit 8 retreats from the optical path. When the alignment and the focus between the optical unit and the subject's eye E are properly adjusted, the operator can push the shooting switch to perform shooting. At the time of shooting, a light flux of white light emitted from the flash tube 4 travels through the folding mirror 6 and the first and second relay lenses 7 and 9, is reflected on the perforated mirror 10, and forms ring-shaped flash light. The reflected ring-shaped flash light illuminates the fundus Er through the pupil of the subject's eye E. The reflection light from the fundus Er passes the photographic diaphragm 12 of the perforated mirror 10, travels through the focus lens 14 and the imaging lens 15, and reaches the imaging unit 17 behind the quick return mirror 16 which is pulled upward out of the optical path, so that the fundus image Ef can be photographed.

If the alignment driving unit can drive at least only in the operation distance direction, the fundus camera can be automatically positioned to the proper operation distance by detecting the proper operation distance and feeding back the detected result to an alignment driving system as described above.

When the positional relationship between the subject's eye E and the optical unit deviates vertically or horizontally, it can be recognized that the bright spot image A deviates vertically or horizontally on the imaging plane of the imaging unit 17. By performing such detection, the positional deviations can be recognized in a three-dimensional direction in addition to the operation distance direction, and an automatic alignment can be implemented by performing feedback control to position the alignment driving unit at the proper position according to the amount of deviation.

Figure 10:
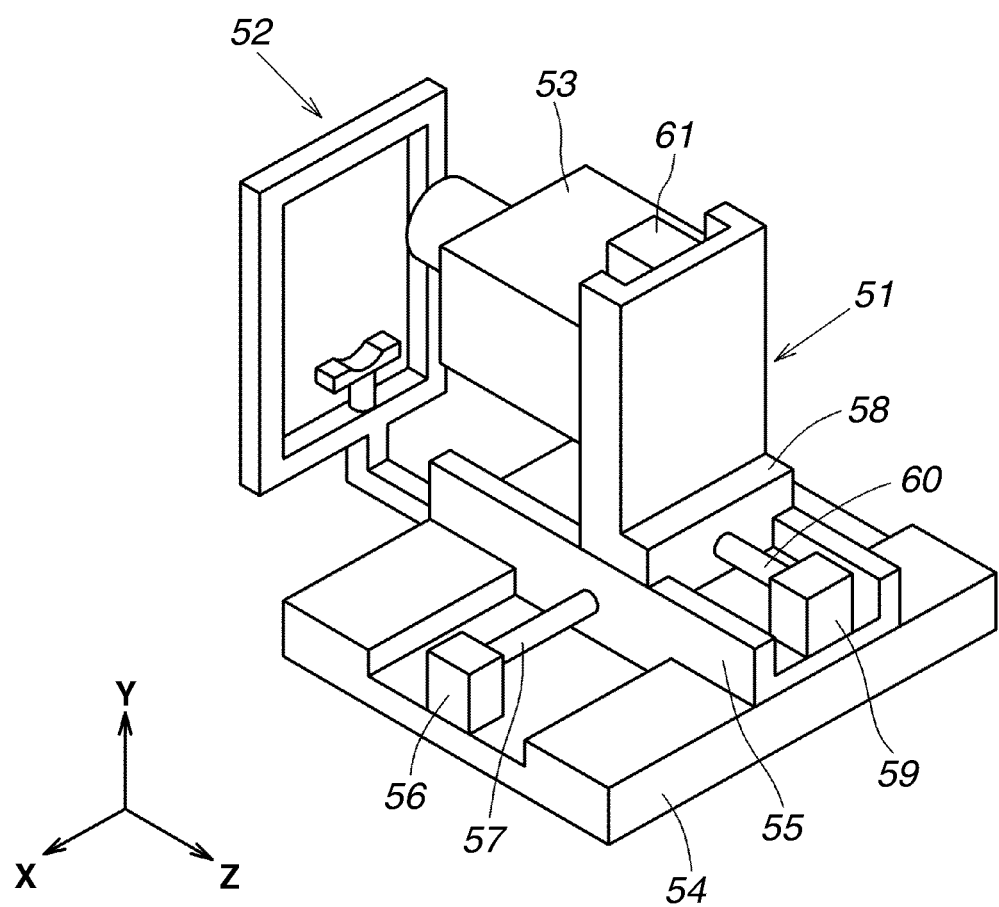
FIG. 10 is a perspective view illustrating a fundus camera including an alignment driving mechanism.

FIG. 10 illustrates a perspective view of a fundus camera including the above described alignment driving mechanism according to a second exemplary embodiment. The fundus camera includes a main body unit 51 and a face fixation unit 52 for a subject. The main body unit 51 includes an optical unit 53 with a built-in optical system, and three optical unit driving units which move the optical unit 53 in X, Y, and Z axial directions in the three-dimensional space. A groove is formed in the X axial direction on a fixation unit 54 which is a base, and a movable unit 55 is inserted into the groove. A female screw portion which is drilled in the movable unit 55 engages with a male threaded rod 57 of a driving motor 56 fixed at the fixation unit 54.

Similarly, a groove is formed in the Z axial direction on the movable unit 55, and a movable unit 58 is inserted into the groove. The movable unit 58 engages with a driving motor 59 fixed on the movable unit 55 via a threaded rod 60. Further, a groove is formed in the Y axial direction on the movable unit 58, and the optical unit 53 is inserted into the groove. The optical unit 53 engages with a driving motor 61 on the movable unit 58 via a threaded rod (not illustrated).

These driving motors 56, 59, and 61 are electrically connected to a below described calculation control circuit, so that the driving motors 56, 59, and 61 can control the optical unit 53 to move to predetermined positions in the three-dimensional direction. The driving motors 56, 59, and 61 can be selected from pulse motors and DC motors, for example. However, when a DC motor which cannot quantitatively control rotation is used, it is desirable that an apparatus internally includes a detection element which can detect a position by detecting a movement distance of the optical unit driving unit and a rotation amount of the driving motor.

Figure 11:
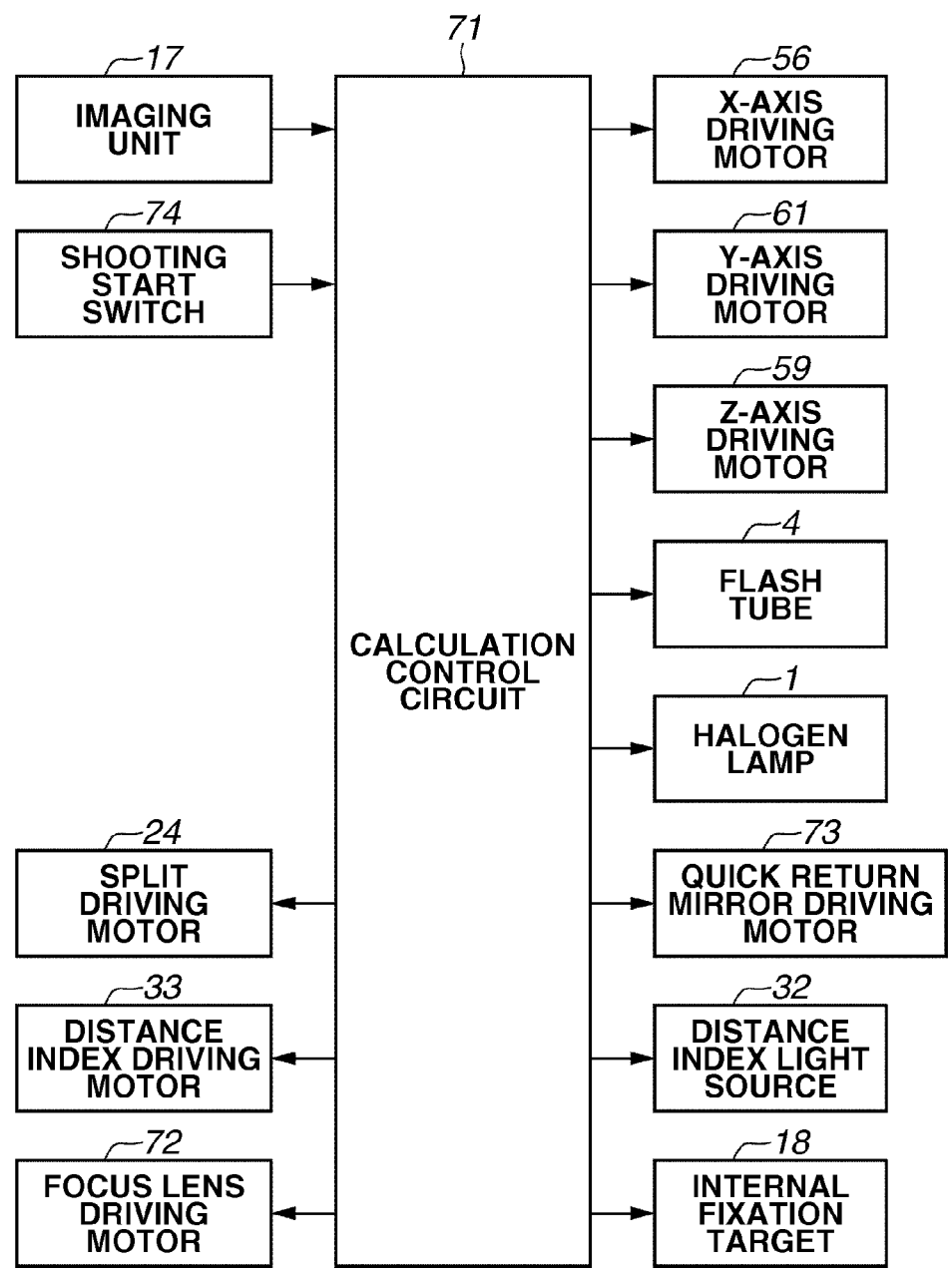
FIG. 11 illustrates a block circuit configuration of a second exemplary embodiment.

FIG. 11 illustrates a block circuit configuration for performing motor control for automatic alignment. Outputs of a calculation control circuit 71 are connected to the driving motors 56, 59, and 61, a driving motor 72 for driving the focus lens 14, the split driving motor 24, the distance index driving motor 33, and a quick return mirror driving motor 73 via respective driver circuits. Further, the output of the calculation control circuit 71 is connected to the halogen lamp 1, the flash tube 4, the distance index light source 32, and the internal fixation target 18. Furthermore, outputs of the imaging unit 17 and a shooting start switch 74 are connected to the calculation control circuit 71.

At the time of automatic alignment, a video signal of the bright spot image A acquired by the imaging unit 17 which is arranged in the optical unit 53 is input to the calculation control circuit 71. In addition to the detection of the operation distance as described above, the calculation control circuit 71 calculates a deviation amount of the bright spot image A in the vertical and horizontal directions from the predetermined position on the imaging plane, and transmits a signal to the driving motors 56, 59, and 61 provided at the optical unit driving unit so that the bright spot image A is on a predetermined position. The driving motor 56, 59, and 61 electrically move the optical unit 53 in the vertical and horizontal directions based on the signal received from the calculation control circuit 71, and perform alignment to a proper position with respect to the subject's eye E.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-183339 filed Aug. 6, 2009, which is hereby incorporated by reference herein in its entirety.

What is claimed is:

1. An ophthalmologic apparatus comprising;
an index projection unit configured to project an index on a cornea of a subject's eye;
an imaging unit configured to form an image on an imaging plane via an objective lens and capture an image of the index projected on the cornea;
a driving unit configured to move a light-emitting surface of the index projection unit so as to change a size of the index; and
a control unit configured to control a distance between the subject's eye and the object lens based on a size of the captured index.

2. The ophthalmologic apparatus according to claim 1, wherein a movement of the light emitting surface by the driving unit is a reciprocation movement.

3. The ophthalmologic apparatus according to claim 2, wherein the control unit controls the distance based on a relation between the size of the captured index and the distance from the light-emitting surface of the index projection unit to the subject's eye.

4. The ophthalmologic apparatus according to claim 1, further comprising:
an illumination optical system configured to project a ring-shaped illumination light on a pupil of the subject eye; and an imaging optical system configured to form an image of a light flux of the illumination light reflected from a fundus on the imaging plane via an object lens and capture a fundus image.

5. The ophthalmologic apparatus according to claim 4, wherein the illumination optical system comprises a perforated mirror configured to reflect illumination light, and wherein the index projection unit is disposed in a hole portion of the perforated mirror.

6. The ophthalmologic apparatus according to claim 1, wherein the control unit obtains a working distance for the subject eye based on a size of a shape of the index captured at at least three positions with different distances from the light-emitting surface to the subject's eye.

7. An ophthalmologic apparatus comprising;
   an index projection unit configured to project an index on a cornea of a subject's eye;
   an imaging unit configured to form an image on an imaging plane via an objective lens and capture an image of the index projected on the cornea; and
   a control unit configured to control a distance between the subject's eye and the object lens so that a size of the captured index becomes a predetermined size
   wherein the control unit obtains a working distance for the subject eye based on a size of a shape of the index captured at a plurality of positions with different distances from the light-emitting surface to the subject's eye.

8. The ophthalmologic apparatus according to claim 7, further comprising:
   a driving unit configured to move a light-emitting surface of the index projection unit so as to change the size of the index,
   wherein a movement of the light emitting surface by the driving unit is a reciprocation movement.

9. The ophthalmologic apparatus according to claim 8, wherein the control unit controls the distance based on a relation between the size of the captured index and the distance from the light-emitting surface of the index projection unit to the subject's eye.

10. The ophthalmologic apparatus according to claim 7, further comprising:
    an illumination optical system configured to project a ring-shaped illumination light on a pupil of the subject eye; and
    an imaging optical system configured to form an image of a light flux of the illumination light reflected from a fundus on the imaging plane via an object lens and capture a fundus image.

11. The ophthalmologic apparatus according to claim 10, wherein the illumination optical system comprises a perforated mirror configured to reflect illumination light, and
    wherein the index projection unit is disposed in a hole portion of the perforated mirror.

* * * * *